(12) United States Patent
Nakakimura

(10) Patent No.: US 10,598,639 B2
(45) Date of Patent: Mar. 24, 2020

(54) THREE-DIMENSIONAL SPECTRAL DATA PROCESSING DEVICE AND PROCESSING METHOD

(71) Applicant: Shimadzu Corporation, Kyoto (JP)

(72) Inventor: Yuriko Nakakimura, Kyoto (JP)

(73) Assignee: Shimadzu Corporation, Nishinokyo-Kuwabaracho, Nakagyo-ku, Kyoto-shi, Kyoto (JP)

( * ) Notice: Subject to any disclaimer, the term of this patent is extended or adjusted under 35 U.S.C. 154(b) by 57 days.

(21) Appl. No.: 15/536,477

(22) PCT Filed: Jan. 26, 2015

(86) PCT No.: PCT/JP2015/051966
§ 371 (c)(1),
(2) Date: Jun. 15, 2017

(87) PCT Pub. No.: WO2016/120958
PCT Pub. Date: Aug. 4, 2016

(65) Prior Publication Data
US 2017/0356889 A1 Dec. 14, 2017

(51) Int. Cl.
*G01N 30/86* (2006.01)
*H01J 49/00* (2006.01)
*G01N 30/72* (2006.01)

(52) U.S. Cl.
CPC ......... *G01N 30/86* (2013.01); *G01N 30/8682* (2013.01); *H01J 49/0036* (2013.01);
(Continued)

(58) Field of Classification Search
CPC ...... G01N 3/86; G01N 30/86; G01N 30/8682; G01N 30/72; G01N 30/7206; G01N 30/7233
See application file for complete search history.

(56) References Cited

U.S. PATENT DOCUMENTS

2014/0183353 A1* 7/2014 Shimada ............. H01J 49/0036
250/282
2014/0303903 A1* 10/2014 Fujita .................. H01J 49/0036
702/23

FOREIGN PATENT DOCUMENTS

JP 2014-202582 A 4/2013

OTHER PUBLICATIONS

Multivariate analysis enabling profiling and mixed system quantification ~, Shimadzu Corporation, [Search on Dec. 18, 2008 (Heisei 26)], Internet <URL: http://www.an.shimadzu.co.jp/apl/chemometrics.

(Continued)

*Primary Examiner* — Matthew G Marini
(74) *Attorney, Agent, or Firm* — Muir Patent Law, PLLC

(57) ABSTRACT

When performing an analysis of the difference between a specific sample group and a nonspecific sample group, a principle component analysis processing unit (33) performs principle component analysis on a collection of a plurality of mass spectrums created from data obtained for a single specific sample, and a characteristic spectrum acquisition unit (34) acquires a characteristic spectrum for each of a plurality of principle components using factor loadings. A spectrum similarity calculation unit (35) calculates the similarities between all mass spectrums and the characteristic spectrum for each sample, and obtains a representative value for the same. The similarity representative value for each sample is obtained for all the characteristic spectrums. A difference determination unit (36) checks whether there is a significant difference between the distribution of the similarity representative values of the specific sample group and the distribution of the similarity representative values of the nonspecific sample group and determines that the characteristic spectrum which is the source of the similarities having a significant difference is a difference spectrum. The (Continued)

difference spectrum reflects component information characterizing a sample group difference, so a component identification unit (37) searches for the difference spectrum in a library to identify a component. This makes it possible to perform different analysis without performing spectrum peak detection.

6 Claims, 9 Drawing Sheets

(52) U.S. Cl.
CPC ......... *G01N 30/72* (2013.01); *G01N 30/7206* (2013.01); *G01N 30/7233* (2013.01)

(56) References Cited

OTHER PUBLICATIONS

International Search Report of PCT/JP2015/05966 dated Aug. 4, 2016.
Written Opinion of the International Search Authority of PCT/JP2015/05966 dated Aug. 4, 2016.

\* cited by examiner

|  | RT=0.0<br>m/z=300.0000 | RT=0.0<br>m/z=300.2305 | .... | RT=0.1<br>m/z=301.0005 | .... |
|---|---|---|---|---|---|
| Sample A | 10.05 | 11.67 | .... | 15.98 | .... |
| Sample B | 12.89 | 13.56 | .... | 11.23 | .... |
| .... | | | | | |

FIG. 10

THREE-DIMENSIONAL SPECTRAL DATA PROCESSING DEVICE AND PROCESSING METHOD

TECHNICAL FIELD

The present invention relates to a three-dimensional spectral data processing device and a three-dimensional spectral data processing method for processing three-dimensional spectral data from which spectrums, such as mass spectrums and absorption spectrums, indicating the relationship between a predetermined parameter and a signal intensity value can be obtained according to changes of other parameters such as a time and a spatial position.

More specifically, it relates to a three-dimensional spectral data processing device and a three-dimensional spectral data processing method for performing analysis based on, for example, similarities or dissimilarities of a plurality of three-dimensional spectral data obtained from different samples.

The present invention is preferably used to process three-dimensional spectral data obtained by, for example, a Liquid Chromatograph Mass Spectrometer (LC-MS), a Gas Chromatograph Mass Spectrometer (GC-MS), a liquid chromatograph using a multichannel type detector such as, e.g., a photodiode array (PDA) detector, a liquid chromatograph or a gas chromatograph using an ultraviolet-visible spectrophotometer or an infrared spectrophotometer capable of wavelength scanning as a detector, or an imaging mass spectrometer, etc.

BACKGROUND TECHNIQUE

In a liquid chromatograph mass spectrometer (LC-MS), by repeating a scan measurement in a predetermined mass-to-charge ratio m/z range in a mass spectrometer as a detector, a mass spectrum indicating a relationship between a mass-to-charge ratio and a signal intensity can be obtained from moment to moment. Further, in a liquid chromatograph using a PDA detector as a detector, it is possible to obtain an absorption spectrum indicating a relationship between a wave number, a wavelength, etc., and a signal intensity (absorbance) from moment to moment. In this specification, data constituting spectrums such as a plurality of mass spectrums or absorption spectrums obtained according to changes of parameters such as time will be referred to as three-dimensional spectral data.

FIG. 9A is a schematic diagram of three-dimensional spectral data obtained by an LC-MS. Three-dimensional spectral data in this case denotes data having three dimensions: a mass-to-charge ratio m/z which is a unit axis of a mass spectrum; a signal intensity (ion intensity) of a mass spectrum; and a time (retention time RT).

By the way, in various fields such as biochemistry, food, and environmental fields, in order to search for characteristic components from a complicated sample including multiple components or to examine the content of the component, differential analysis by profiling (multivariate analysis) is used (see Non-Patent Document 1). In difference analysis using three-dimensional spectral data obtained from each sample, generally, features such as a peak height, a peak area, etc., are initially extracted from three-dimensional spectral data to create characteristic data. Then, for the two-dimensional characteristic data table in which the characteristic data created for each sample is arranged in a table format, multivariate analysis such as principle component analysis is performed, and from the result, the similarities, etc., of multiple samples are grasped.

A conventional method of creating a two-dimensional characteristic data table from three-dimensional spectral data of a plurality of samples will be described. Based on three-dimensional spectral data as shown in FIG. 9A, when the mass spectrum at the retention time RT=0.00, for example, is extracted, the mass spectrum as shown in FIG. 9B is obtained. For such mass spectrum, peak detection is performed according to predetermined conditions, and the height (intensity value) or peak area (integral value of intensity) of each detected peak is obtained. Then, the mass-to-charge ratio and the peak height (or area) of each peak appearing in the mass spectrum are collected as peak information.

By performing the same processing for all mass spectrums obtained over the entire retention time from the start of measurement to the end of measurement, peak information on all peaks appearing in all mass spectrums is obtained. Based on this peak information, as shown in FIG. 10, a two-dimensional characteristic data table showing the peak height (or area) for the mass-to-charge ratio and retention time of each peak is created for each sample. In this table, when there is no peak (not detected) at a certain mass-to-charge ratio and a certain retention time in a certain sample, the peak height corresponding to the mass-to-charge ratio and retention time may be set to zero.

In an LC and a GC (especially LC), even if the composition separation conditions in the column are set to be equal, the retention time of the same component may sometimes somewhat differs due to factors such as the difference in measurement environment and systematic errors of the device, in other words, a retention time shift may sometimes occur. For this reason, prior to creating a two-dimensional characteristic data table according to the procedure as described above, it is sometimes necessary to perform alignment processing in the retention time direction (processing to adjust the retention time) (see Patent Document 1).

Multivariate analysis such as principle component analysis is performed using the two-dimensional characteristic data table created as described above, and based on the result, for example, a large number of samples are classified into a plurality of groups, and further, components characterizing the difference are identified.

PRIOR ART

Patent Document

Patent Document 1: Japanese Unexamined Patent application Publication No. 2014-202582

Non-Patent Document

Non-Patent Document 1: "Multiprofiling (multivariate analysis)~Multivariate analysis enabling profiling and mixed system quantification~", Shimadzu Corporation, [Search on Dec. 18, 2008 (Heisei 26)], Internet<URL:http://www.an.shimadzu.co.jp/apl/chemometrics/>

SUMMARY OF THE INVENTION

Problems to be Solved by the Invention

As described above, in the conventional difference analysis, when characteristic data is obtained from three-dimensional spectral data to create a two-dimensional characteristic data table, it is necessary to perform peak detection on spectrum and extract peak information. Therefore, there are the following problems.

(1) For algorithms for detecting peaks in a spectrum waveform, various algorithms are known. Even for the same spectrum waveform, peaks to be detected are different depending on the type of algorithm. Therefore, depending on the type of peak detection algorithm, the obtained characteristic data changes, and therefore the result of multivariate analysis to the two-dimensional characteristic data table created based thereon will also differ.

(2) Whatever the algorithm is, it is necessary to set a detection condition, such as, e.g., an intensity threshold, when a peak detection is performed. However, if the condition is inappropriately set, it is impossible to detect an accurate peak, and therefore there are possibilities that important peaks are overlooked or peaks which are not originally peaks are erroneously detected.

(3) If the number of peaks appearing in a spectrum is too many, the data amount of the two-dimensional characteristic data table becomes enormous, and therefore appropriate results may not be obtained by multivariate analysis.

(4) In the system using an LC and a GC, in order to perform accurate peak detection in the spectrum unit, alignment processing in the retention time direction is necessary as described above. If such alignment processing is insufficient, the two-dimensional characteristic data table becomes inaccurate, and therefore appropriate results cannot be obtained by multivariate analysis. To avoid this, an analyst himself/herself has to confirm three-dimensional spectral data or a two-dimensional characteristic data table and correct it manually.

The above problems are mainly caused by peak detection in spectrum units. The present invention was made to solve such problems. It is an object of the present invention to provide a three-dimensional spectral data processing device and processing method capable of obtaining an accurate multivariate analysis result based on a plurality of three-dimensional spectral data without performing peak detection in spectrum units.

Means for Solving the Problems

A three-dimensional spectral data processing device according to the present invention to solve the aforementioned problems is configured to process three-dimensional spectral data constituting a plurality of spectrums each indicating a relationship between a first parameter and a signal intensity and obtained in accordance with a change of a second parameter, the three-dimensional spectral data processing device being configured to analyze similarity or difference between respective three-dimensional spectral data obtained from a plurality of samples. The three-dimensional spectral data processing device includes:

a) a characteristic spectrum acquisition unit configured to perform multivariate analysis by considering a plurality of spectrums constituting a single three-dimensional spectral data obtained from a specific sample among a plurality of samples as a collection of a single spectrum not depending on a value of the second parameter, and based on a result of the multivariate analysis, one or a plurality of characteristic spectrums that characterize the specific sample is obtained;

b) a spectrum similarity calculation unit configured to calculate a similarity between each spectrum for each second parameter value extracted from the three-dimensional spectral data for a single sample and a single characteristic spectrum for each of the one or the plurality of characteristic spectrums obtained by the characteristic spectrum acquisition unit for each of three-dimensional spectral data for a plurality of samples and calculate a representative value of the similarity corresponding to the sample from the plurality of similarities; and c) a difference spectrum determination unit configured to check whether or not there is a significant difference capable of distinguishing between a specific sample and a nonspecific sample based on the representative value of the similarity obtained respectively corresponding to a plurality of samples for each of the characteristic spectrums and determine the characteristic spectrum capable of obtaining the similarity with a significant difference as a difference spectrum.

A three-dimensional spectral data processing method according to the present invention to solve the aforementioned problems is configured to process three-dimensional spectral data constituting a plurality of spectrums each indicating a relationship between a first parameter and a signal intensity and obtained in accordance with a change of a second parameter, the three-dimensional spectral data processing method being configured to analyze similarity or difference between respective three-dimensional spectral data obtained from a plurality of samples. The three-dimensional spectral data processing method includes:

a) a characteristic spectrum acquisition step of performing multivariate analysis by considering a plurality of spectrums constituting a single three-dimensional spectral data obtained from a specific sample among a plurality of samples as a collection of a single spectrum not depending on a value of the second parameter, and based on a result of the multivariate analysis, obtaining one or a plurality of characteristic spectrums that characterize the specific sample;

b) a spectrum similarity calculation step of calculating a similarity between each spectrum for each second value extracted from the three-dimensional spectral data for a single sample and a single characteristic spectrum for each of the one or the plurality of characteristic spectrums obtained in the characteristic spectrum acquisition step for each of three-dimensional spectral data for a plurality of samples and calculating a representative value of the similarity corresponding to the sample from the plurality of similarities; and c) a difference spectrum determination step of checking whether or not there is a significant difference capable of distinguishing between a specific sample and a nonspecific sample based on the representative value of the similarity obtained respectively corresponding to a plurality of samples for each of the characteristic spectrums and determining the characteristic spectrum capable of obtaining the similarity with the significant difference as a difference spectrum.

The "three-dimensional spectral data" described herein denotes, for example, data representing a large number of mass spectrums (including $MS^n$ spectrums in which n is 2 or more) obtained with the lapse of time in an LC-MS or a GC-MS, data representing a large number of mass spectrums obtained from a number of different (i.e., different spatial positions) measurement points on a sample in an imaging mass spectrometer, data representing a number of absorbance spectrums obtained with the laps of time in an LC using a PDA detector or a UV-visible spectrophotometer capable of wavelength scanning, data representing a number of absorbance spectrums obtained with the laps of time in a GC using an infrared spectrophotometer as a detector, etc.

In the three-dimensional spectral data processing device according to the present invention, since difference analysis of a plurality of samples is performed, three-dimensional spectral data obtained by measuring each of the plurality of samples is given. However, additional information that one of the plurality of samples is a specific sample containing, for example, a specific component is given separately. That is, this is supervised difference analysis.

The characteristic spectrum acquisition unit considers a plurality of spectrums generated from a single three-dimensional spectral data derived from the specific sample specified by the additional information as a single spectrum collection independent of the value of the second parameter, and performs predetermined multivariate analysis for it. For example, when the three-dimensional spectral data is data obtained by an LC-MS, at the stage of creating a collection of spectrums, information on the second parameter value (corresponding to retention time in an LC-MS) of each mass spectrum is discarded. The multivariate analysis used is typically principle component analysis (PCA), but it is not limited to this. Non-negative matrix factorization (NMF), multivariate curve resolution (MCR), etc., may be used. When principle component analysis is performed on spectrum data collection, derived factor loading is obtained for each first parameter value (e.g., a mass-to-charge ratio) for each derived principal component. Therefore, the relationship between the first parameter and the factor loading amount can be taken as the characteristic spectrum, and therefore the characteristic spectrum is obtained by the number of principle components. In this case, it may be configured such that the principle component number be determined automatically based on the cumulative contribution ratio, etc., or an analyst determine the appropriate number of principle components and sets it by an input operation from the input unit.

Normally, since a plurality of characteristic spectrums are obtained, the spectrum similarity calculation unit calculates the similarity between each spectrum at each measurement time extracted from the three-dimensional spectral data to a single sample and a characteristic spectrum for each of three-dimensional spectral data with respect to a plurality of samples for each characteristic spectrum. Therefore, in one sample, the similarity for a single characteristic spectrum is obtained by the number of spectrums. Therefore, from the plurality of similarities, a representative value of similarity related to a single characteristic spectrum is calculated in one sample. The representative value may be, for example, an average value, a median value, a mode value, a sum value, or a maximum value of a plurality of similarities. As a result, for each sample, the representative value of similarity is obtained by the number of characteristic spectrums for each sample.

Based on the representative value of similarity obtained as described above, the difference spectrum determination unit investigates whether there is a significant difference capable of discriminating between a specific sample and a nonspecific sample contained in a plurality of given samples. The determination of the presence or absence of the significant difference can be made, for example, by using various hypothesis test methods in statistics. It is assumed that a characteristic spectrum showing a distribution in which there is a significant difference between the distribution of the representative value of the similarity of the specific sample group and the distribution of the representative value of the similarity of the nonspecific sample group contains information related to the component corresponding to the difference. Therefore, the difference spectrum determination unit determines the characteristic spectrum capable of obtaining the similarity with a significant difference as a difference spectrum reflecting the difference between the specific sample and the nonspecific sample.

For example, it is presumed that a peak showing large intensity in the difference spectrum is derived from a characteristic component included in the specific sample but not included in the nonspecific sample. Therefore, for example, an analyst finds the mass-to-charge ratio corresponding to the peak of large intensity from the difference spectrum displayed on the display screen, and estimates the component from its mass-to-charge ratio. Of course, it is preferable that such component estimation can be done automatically.

That is, it is preferable that the three-dimensional spectral data processing device according to the present invention further include a database that stores information on compounds; and a component identification unit configured to perform component identification by collating information obtained from the difference spectrum determined by the difference spectrum determination unit with information in the database.

As the database, a general-purpose compound database storing various compounds can be used. Further, in the case of performing analysis for a specific purpose in which the type of sample is limited, it is preferable to use a database storing compounds corresponding to the purpose. According to the above configuration, even if a component characterizing a specific sample is unknown, such a component can be automatically specified by difference analysis.

Further, in the three-dimensional spectral data processing device according to the present invention, it may be configured to further include a display configured to display the difference spectrum determined by the difference spectrum determination unit and the distribution status of representative values of similarity in all samples for the difference spectrum.

According to the configuration, an analyst can not only visually recognize the difference spectrum presumed to correspond to the component characterizing the specific sample, but also judge the reliability of the difference spectrum from the distribution situation of the similarity representative values.

Effects of the Invention

According to the three-dimensional spectral data processing device and processing method of the present invention, without detecting characteristic data by performing peak detection on three-dimensional spectral data as in the past, it is possible to accurately perform difference analysis on two groups: a specific sample groups including a specific component; and a sample group not including the specific component, and search the spectrum corresponding to the component. Therefore, it is possible to avoid an error of difference analysis due to a difference of kinds of peak detection algorithms, inappropriate setting of peak detection condition, etc. The accuracy of component estimation using the spectrum obtained with difference analysis can also be improved.

Further, in the three-dimensional spectral data processing device and processing method according to the present invention, since a second parameter such as a retention time, etc., is not taken into account when determining the characteristic spectrum, no alignment processing is required for aligning the retention time among a plurality of samples which are normally required when obtaining a two-dimensional characteristic data table including characteristic data for a plurality of samples, and the time and effort required for such processing can be saved. As a result, the throughput of the whole difference analysis can be improved.

BRIEF DESCRIPTION OF THE DRAWINGS

FIG. 10 is an example of a two-dimensional characteristic data table created based on three-dimensional mass spectrum data.

EMBODIMENT FOR CARRYING OUT THE INVENTION

Figure 1:
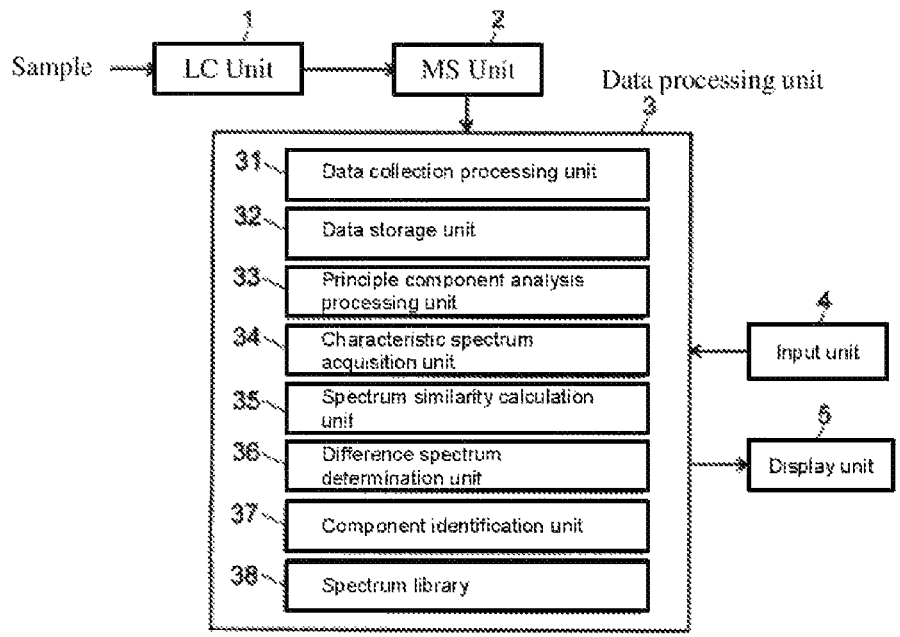
FIG. 1 is a schematic configuration diagram of an example of an LC-MS system equipped with a three-dimensional spectral data processing device according to the present invention.

An embodiment of an LC-MS system equipped with a three-dimensional spectral data processing device according to the present invention will be described with reference to the accompanying drawings.

In the LC-MS system of the present embodiment, although not shown, an LC unit 1 includes a liquid feeding pump for feeding a mobile phase at a constant flow rate, an injector for injecting a sample into the mobile phase to be fed, a column for separating components in the sample in the time direction, and the like. Further, the MS unit 2 is, for example, a time-of-flight mass spectrometer equipped with an electrospray ion source. Samples containing components separated in the time direction in the LC unit 1 are sequentially introduced into the MS unit 2. In the MS unit 2, ions derived from components contained in the sample to be introduced are detected.

The detection signal obtained by the MS unit 2 is input to a data processing unit 3. In order to perform characteristic processing to be described later, the data processing unit 3 includes, as functional blocks, a data collection processing unit 31, a data storage unit 32, a principle component analysis processing unit 33, a characteristic spectrum acquisition unit 34, a spectrum similarity calculation unit 35, a difference spectrum determination unit 36, a component identification unit 37, and a spectrum library 38. To this data processing unit 3, an input unit 4 for conducting various input operations by an analyst and a display unit 5 for displaying processing results, etc., are connected. Most of the functions of the data processing unit 3 can be realized by operating dedicated data processing software installed in a personal computer.

Figures 9A, 9B:
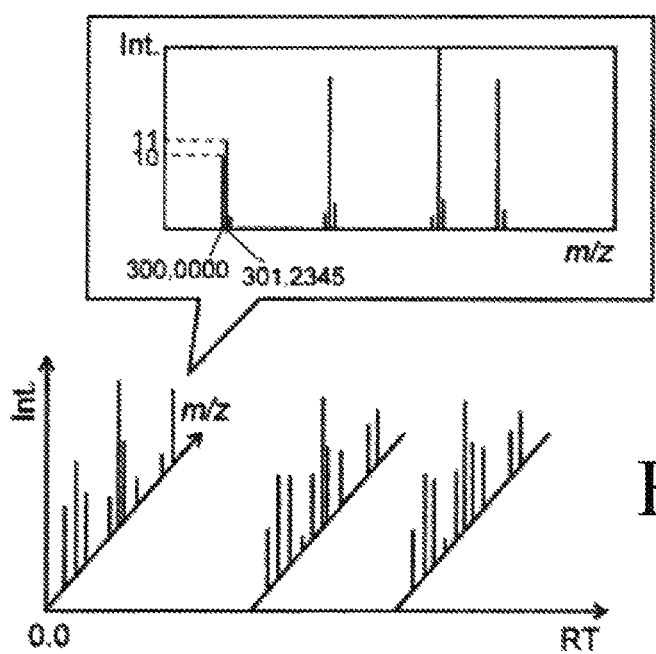
FIG. 9A is a schematic diagram of three-dimensional mass spectrum data obtained by an LC-MS.
FIG. 9B is a diagram showing one mass spectrum.

In the LC-MS system of this embodiment, by performing a measurement on the sample at the measuring unit including the LC unit 1 and the MS unit 2, as the time elapses from the time when the sample is introduced into the LC unit 1, detection signals can be obtained. The data collection processing unit 31 converts the input detection signals into digital data and stores them in the data storage unit 32. Three-dimensional mass spectrum data as shown in, for example, FIG. 7A (the same as FIG. 9A) is obtained by the measurement with respect to one sample. In the case of performing comprehensive analysis by multivariate analysis, measurements are performed on a large number of samples as analysis objects, respectively, and three-dimensional mass spectrum data corresponding to each sample is stored in the data storage unit 32.

Characteristic data processing in the LC-MS system of this embodiment, which is executed in a state in which the three-dimensional mass spectrum data corresponding to a plurality of samples is stored in the data storage unit 32 as described above, will be described.

Figure 2:
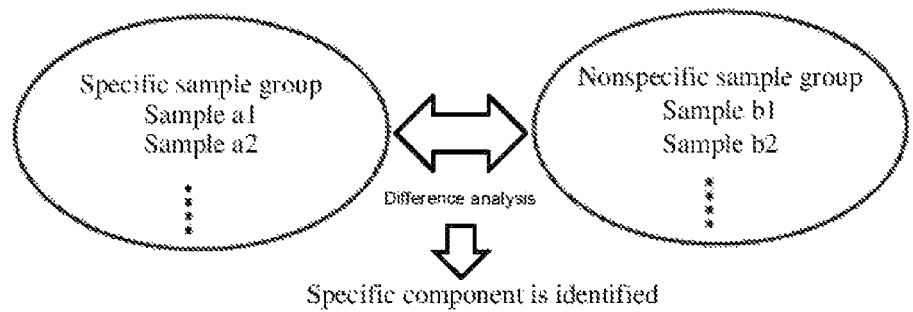
FIG. 2 is a conceptual diagram of difference analysis.

FIG. 2 is a conceptual diagram of the difference analysis assumed here.

A number of samples to be measured include samples a1, a2, ..., which are known that specific components are contained and samples b1, b2, ..., which are known that no specific components are contained. As shown in the figure, these samples are classified into a specific sample group and a nonspecific sample group, and it is assumed that each sample is labeled as belonging to one of the groups. However, it is unknown what the specific component is. Here, the purpose of the analysis is to make difference analysis between samples contained in two groups, a specific sample group and a nonspecific sample group, to identify the component characterizing the difference, that is, the aforementioned specific component.

Figure 3:
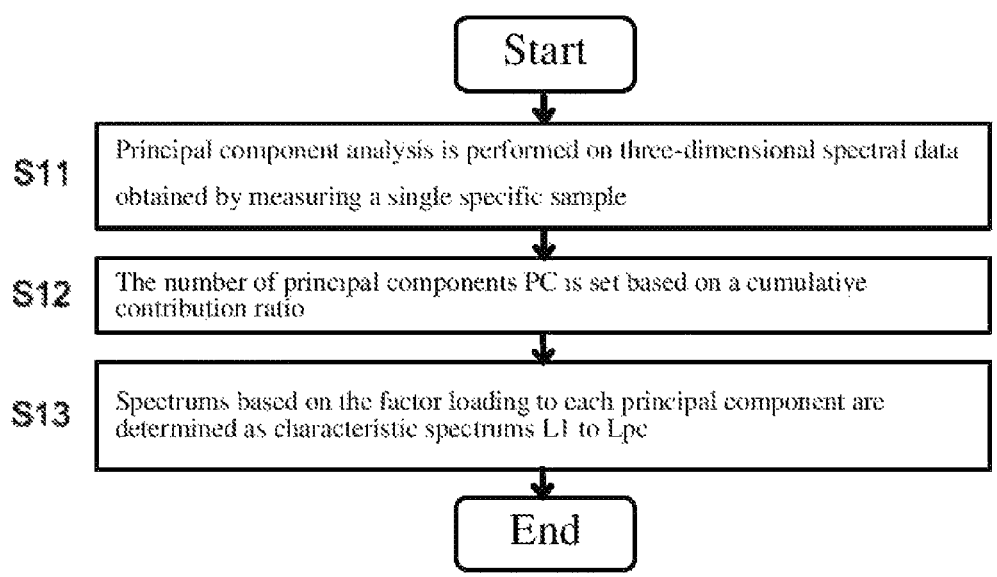
FIG. 3 is a flowchart showing a procedure of characteristic spectrum acquisition processing in the LC-MS system of the present embodiment.
Figure 4:
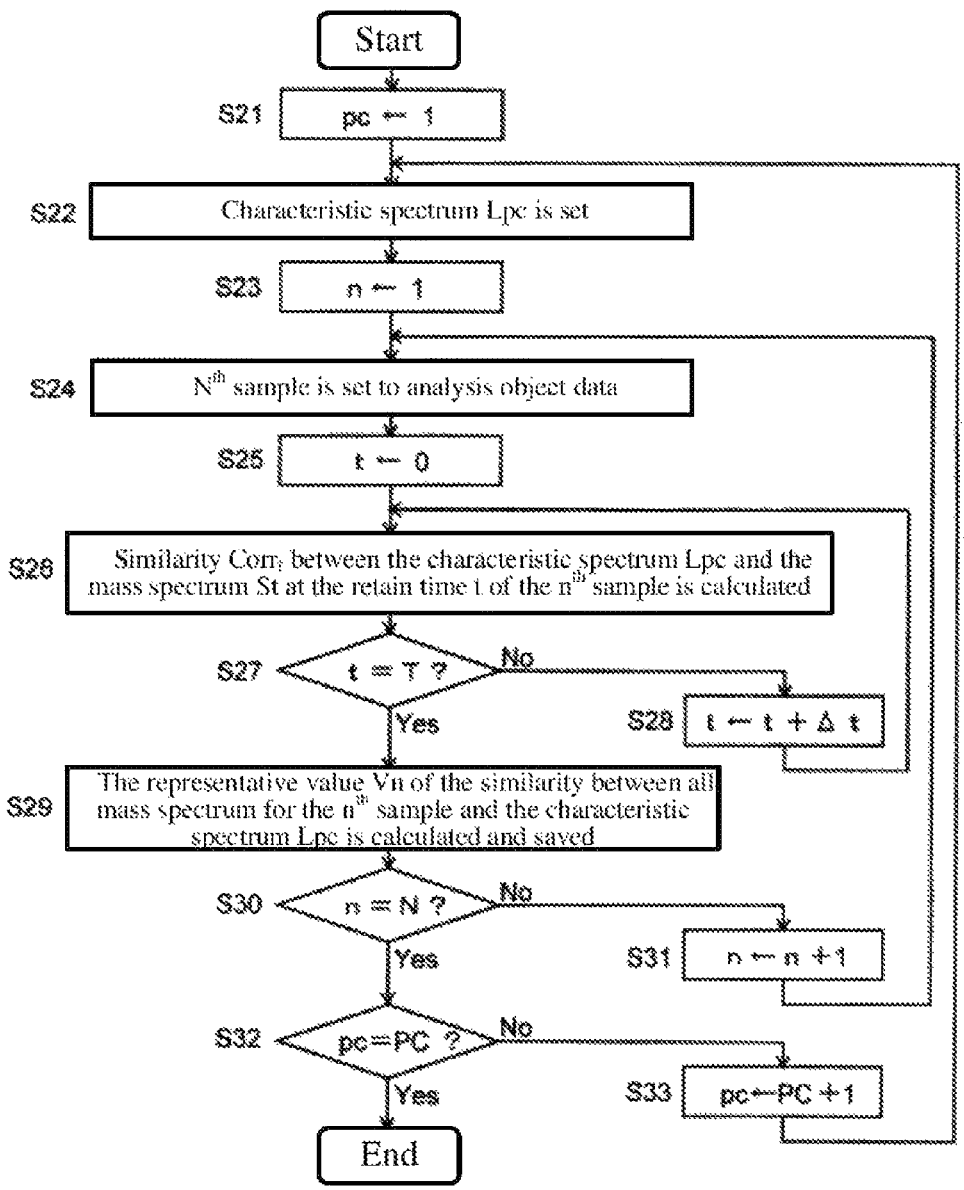
FIG. 4 is a flowchart showing a procedure of spectrum similarity calculation processing in the LC-MS system of the present embodiment.
Figure 5:
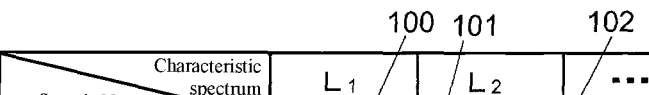
FIG. 5 shows a similarity representative value table obtained by the spectrum similarity calculation processing.
Figure 6:
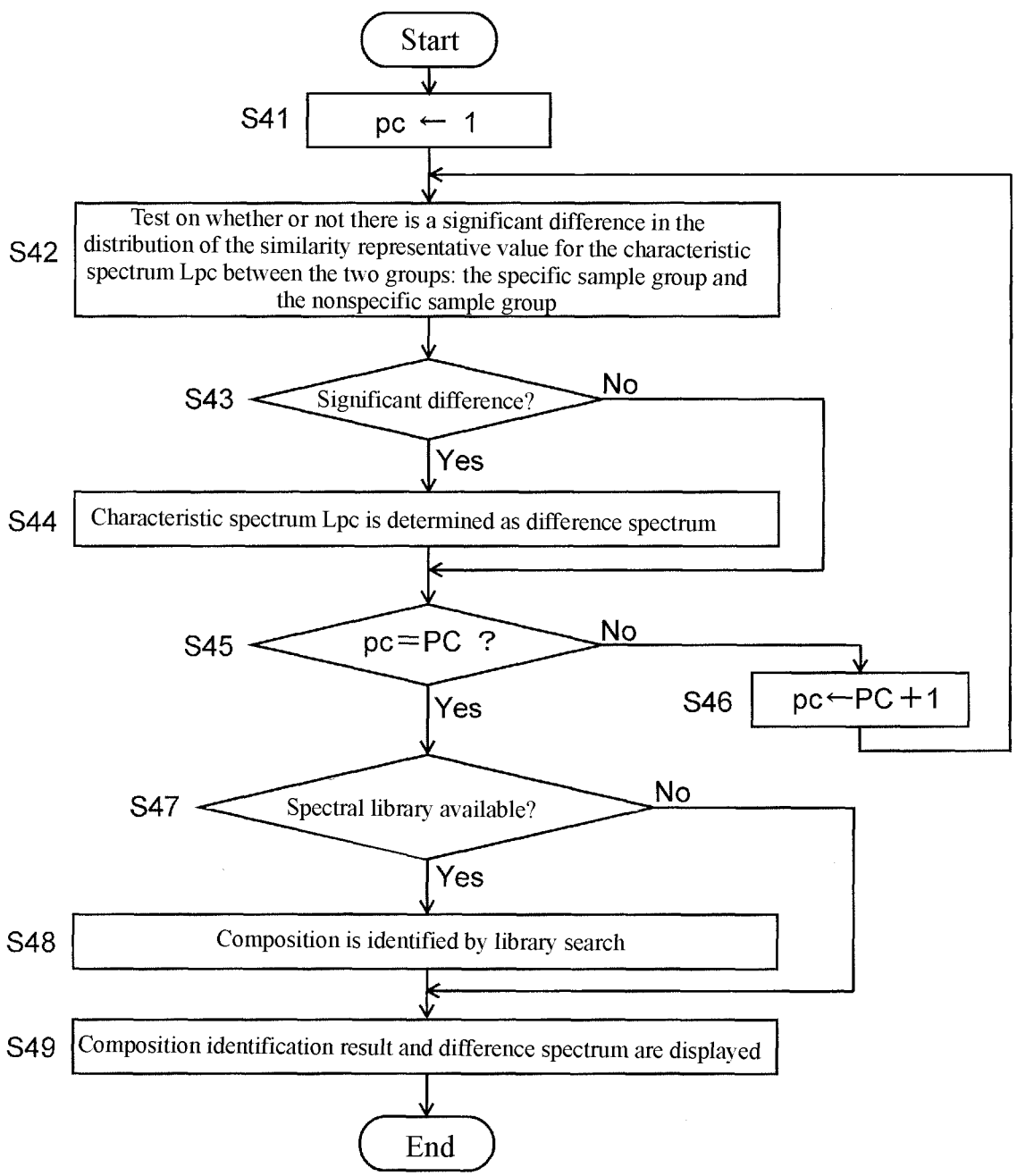
FIG. 6 is a flowchart showing a procedure of difference spectrum determination processing in the LC-MS system of the present embodiment.

FIG. 3 is a flowchart showing a procedure of characteristic spectrum acquisition processing. FIG. 4 is a flowchart showing a procedure of spectrum similarity calculation processing. FIG. 6 is a flowchart showing a procedure of difference spectrum processing. Further, FIG. 7 is an explanatory diagram of characteristic spectrum acquisition processing and spectrum similarity calculation processing. FIG. 5 is a diagram showing a similarity representative value table obtained by the spectrum similarity calculation processing.

For example, when an analyst instructs execution of the difference analysis from the input unit 4, in the data processing unit 3, characteristic spectrum acquisition processing is performed in the procedure shown in FIG. 3.

Figure 7D:
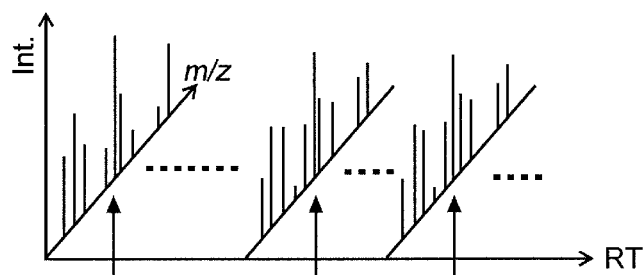
FIG. 7A-D is an explanatory diagram of characteristic spectrum acquisition processing and spectrum similarity calculation processing.
Figure 7C:
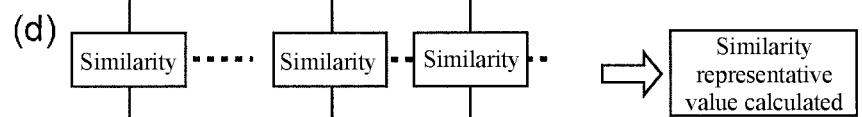
Figure 7C:
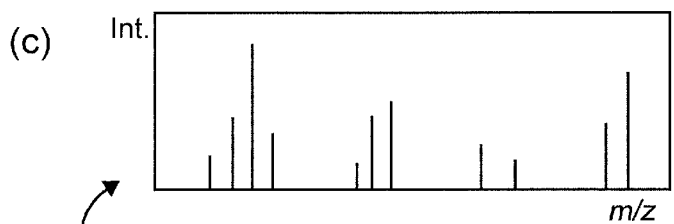
Figure 7B:
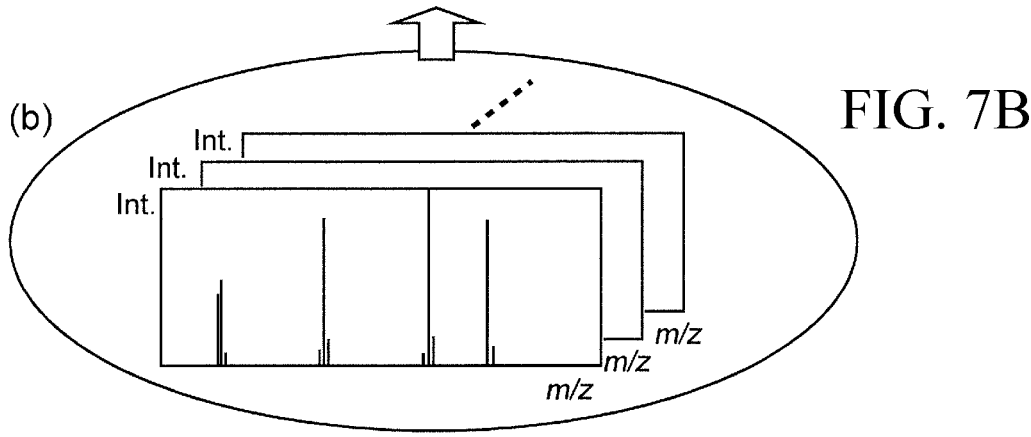
Figure 7A:
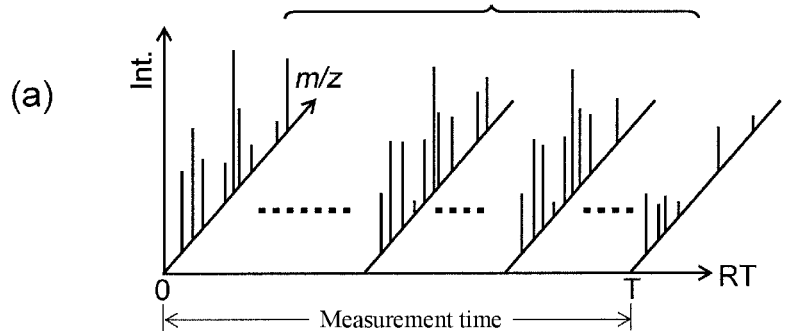

That is, the principle component analysis processing unit 33 reads out three-dimensional mass spectrum data corresponding to one of the samples labeled with a specific sample group from the data storage unit 32 and performs principle component analysis on this data (Step S11). It is desirable that one sample selected here be a sample presumed to be most specific. Therefore, it is advisable that an analyst can specify from the input unit 4 which specific sample to select. As shown in FIG. 7A, the three-dimensional mass spectrum data obtained from the data storage unit 32 includes retention time RT information. However, when principle component analysis is performed in Step S11, three-dimensional mass spectrum data is regarded as a collection of simple mass spectrum data irrelevant to retention time (see FIG. 7B). At this point, the information on retention time is discarded from the three-dimensional mass spectrum data.

The principle component analysis processing unit 33 does not decide the number of principle components in advance and determines the principle component number PC based on the cumulative contribution ratio obtained by the principle component analysis (Step S12). By the principle component analysis, the factor loading amount (principle component loading) for each principle component from the first principle component to the PC principle component is calculated for each mass-to-charge ratio. The characteristic spectrum acquisition unit 34 creates spectrums (see FIG. 7C) in which the factor loadings are arranged on the mass-to-charge ratio axis for each principle component and sets as characteristic spectrums L$1$ to L$_{PC}$ of the specific sample (Step S13). By performing the principle component analysis, it is possible to extract features of the three-dimensional mass spectrum data in the specific sample based on statistics, information of the specific component should be reflected in at least one of the PC characteristic spectrums. At this point, since it is unknown which factor loading for any principle component contains the information of the specific component, what is obtained in Step S13 is a spectrum that may characterize the difference between the specific sample and the nonspecific sample.

In this embodiment, the principle component analysis, which is one method of multivariate analysis, is applied to the mass spectrum collection obtained from the three-dimensional mass spectrum data. However, the method which can be adopted here is not limited to principle component analysis. For example, nonnegative matrix factorization (NMF), multivariate curve resolution (MCR), etc., may be used. Care must be taken in principle component analysis because factor loading may sometimes become a negative value in some cases. However, in multivariate curve resolution, etc., factor loading always becomes a positive value, so it is rather convenient to create a characteristic spectrum.

In the data processing unit 3, spectrum similarity calculation processing is subsequently performed in the procedure shown in FIG. 4. That is, the spectrum similarity calculation unit 35 sets the variable pc designating the principle component to 1 (Step S21), and sets the characteristic spectrum Lpc which is a reference for similarity calculation (Step S22). Next, the variable n designating the sample is set to 1 (Step S23), and the three-dimensional mass spectrum data obtained from the n$^{th}$ sample is set as the data of the analysis object (Step S24). Here, to all of the sample a1, a2, . . . , b1, b2, consecutive numbers are allotted in advance.

Next, the variable t designating the retention time is set to 0 (Step S25), and the mass spectrum St at the retention time t in the three-dimensional mass spectrum data derived from the n$^{th}$ sample, and the similarity Corr$_t$ between the mass spectrum St and the characteristic spectrum Lpc is calculated (Step S26). This similarity Corr$_t$ can be calculated, for example, based on the difference in signal intensity value for each mass-to-charge ratio. In addition, even in cases where the measurement conditions are the same, if the samples are different, the detection sensitivity may be different in some cases. Therefore, before calculating the similarity, for example, it may be configured such that the signal intensity value in one or both spectrums are standardized so that the signal intensity value in a specific mass-to-charge ratio and the signal intensity value with the maximum intensity are aligned.

When the similarity Corr$_t$ between the two spectrums is obtained, it is judged whether or not the variable t has reached the measurement end time T (Step S27). If the variable t has not reached the measurement end time T, the value obtained by adding a data measurement time interval Δt to the variable t is set as a new variable t (Step S 28), and the process returns to Step S 26. Therefore, by repeating Steps S26, S27, and S28, for the specified n$^{th}$ sample, the similarity Corr$_t$ between the characteristic spectrums Lpc will be calculated for all mass spectrums obtained from the variable t from 0 to the measurement end time T, that is, during the entire measurement period from the measurement start time to the measurement end time. As a result, the same number of similarities Corr$_t$ as the number of measurement points is obtained (see FIG. 7D).

When it is determined as "Yes" in Step S27, the spectrum similarity calculation unit 35 calculates and stores the representative value Vn of similarity based on all similarities Corr$_t$ equal to the number of measurement points obtained for the n$^{th}$ sample (Step S29). The representative value Vn is an average value, a median value, a mode value, a sum value, a maximum value, or the like, of all similarities. For example, when n=1 and pc=1, one representative value in the frame 100 enclosed by the solid line in the table shown in FIG. 5 is obtained.

Subsequently, it is determined whether or not the variable n designating the sample has reached the total sample number N (Step S30). If not, the variable n is incremented (Step S31) and the process returns to Step S24. Therefore, by repeating steps S24 to S31, for each of all N samples, a representative value Vn of similarity between a mass spectrum based on three-dimensional mass spectrum data obtained from each sample and one characteristic spectrum Lpc can be obtained. For example, when pc=1, N similarity representative values in the frame 101 surrounded by the one-dot chain line in the table shown in FIG. 5 are obtained.

When it is determined as "Yes" in step S30, next, it is judged whether or not the variable pc designating the principle component has reached the principle component number PC (Step S32). If not, the variable pc is incremented (Step S33) and the process returns to Step S22. Therefore, by repeating Steps S22 to S33, a similarity representative value corresponding to each of N samples is obtained for each of the PC characteristic spectrum Lpc. That is, similarity representative values for (N×PC) number in the frame 102 enclosed by the two-dot chain line in the table shown in FIG. 5, that is, all combinations of samples and characteristic spectrums are obtained. Thus, the similarity representative value table shown in 5 is completed. It is obvious that a procedure different from the procedure shown in FIG. 4 can be used to obtain each similarity representative value that fills the similarity representative value table as described above.

Further, in the data processing unit 3, difference spectrum processing is performed according to the procedure shown in FIG. 6. That is, the difference determination unit 36 first sets the variable pc designating the principle component to 1 (Step S41). Then, using the similarity representative value in the similarity representative value table described above, it is determined whether there is a significant difference in the distribution of the similarity representative values for the characteristic spectrum Lpc between the two sample groups: the specific sample group and the nonspecific sample group (Step S42).

Conventionally known various statistical hypothesis tests may be used to judge the presence or absence of this significant difference.

When it is determined that there is a significant difference in the distribution of the similarity representative values corresponding to the two sample groups by the above test (Yes in Step S43), the characteristic spectrum Lpc at that time is determined as the difference spectrum for the two sample groups (Step S44). On the other hand, when it is determined that there is no significant difference in the distribution of similarity representative values in Step S43, the process of Step S44 is passed. Then, it is determined whether or not the variable pc designating the principle component has reached the principle component number PC (Step S45). If not, the variable pc is incremented (Step S46) and the process returns to Step S42. Therefore, by repeating Steps S42 to S46, for each of the PC characteristic spectrums Lpc, it is judged whether or not there is a significant difference in the distribution of similarity representative values. One or more characteristic spectrums judged to have significant differences are determined as a difference spectrum. As mentioned above, this difference spectrum is considered to be a spectrum including information characterizing a specific component included in the specific sample but not included in the nonspecific sample.

Therefore, the component identification unit 37 determines whether or not the spectrum library 38 is available (Step S47). If available, it identifies the specific component by collating one or more differing spectrums with information in the spectrum library 38 (Step S48). At this time, the mass spectrum pattern (that is, the mass-to-charge ratio of multiple peaks in the mass spectrum) may be checked. However, it may be simply configured such that a mass-to-charge ratio corresponding to a specific peak having a large intensity is obtained from the difference spectrum and is collated with the mass of the compound contained in the spectrum library 38. As such a spectrum library 38, for example, a general-purpose compound database such as Pubchem operated by the National Bioinformatics Center of the United States may be used. Alternatively, a library that contains only specific compounds provided by equipment manufacturers or created by the user himself/herself may be used.

Then, when the component can be identified, the identification result is displayed on the screen of the display unit 5 together with the difference spectrum. Also, if ingredient identification is not possible, it is displayed so. Furthermore, if the spectrum library 38 cannot be used for some reason, only the difference spectrum is displayed (Step S49). In this way, according to the LC-MS system of this embodiment, it is possible to provide analysts with information on difference spectrums derived by difference analysis for two sample groups and information on specific components derived from the difference spectrums.

By creating and displaying a graph showing the distribution of the similarities of all the samples as well as the difference spectrums, it is possible for an analyst to intuitively and easily confirm whether or not the difference spectrum determined in Step S44 is appropriate for identifying a plurality of sample groups.

Figure 8A:
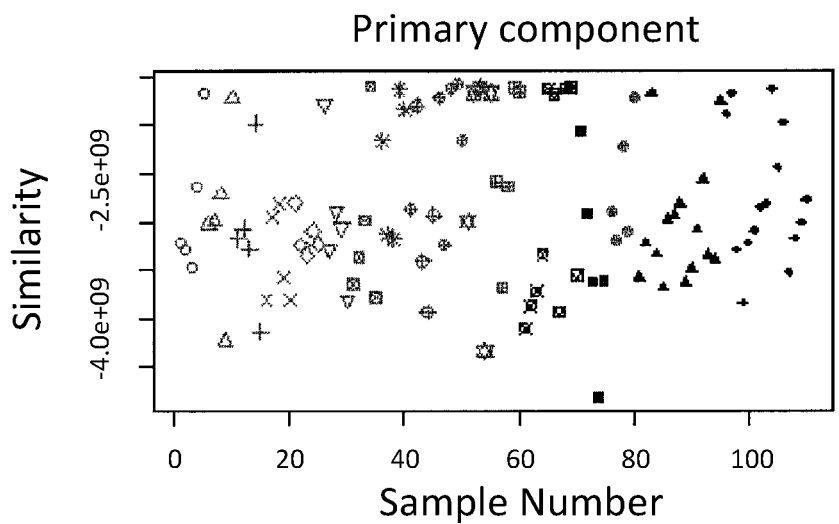
FIG. 8. A-C shows a display example of similarity distributions of all samples.
Figure 8B:
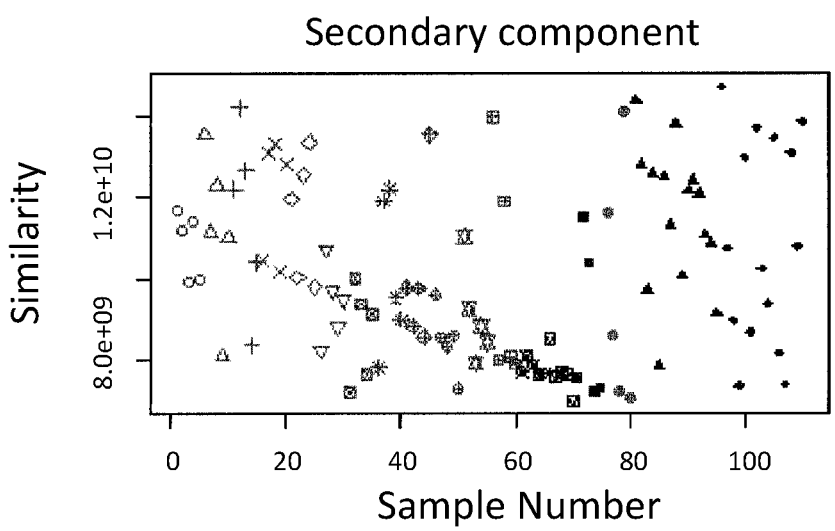
Figure 8C:
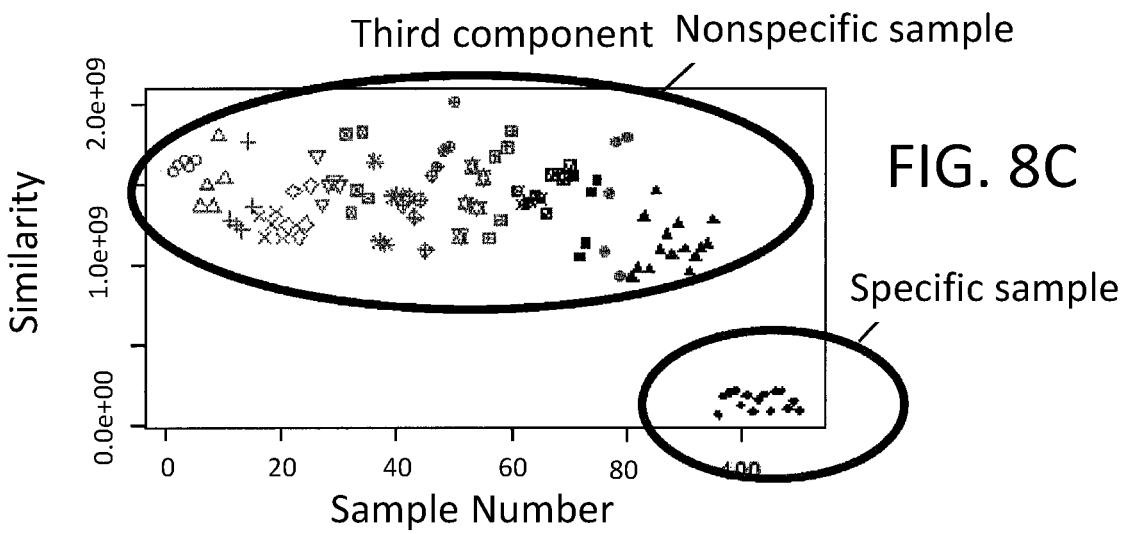

FIG. 8 is an example of a graph showing the distribution of similarities of all samples to the characteristic spectrums of the first to third principle components. In this example, only the characteristic spectrum of the third principle component was determined as the difference spectrum by the test of Step S42. Looking at the distribution of similarities in this third principle component, it can be confirmed also by an analyst that the nonspecific samples and the specific samples are clearly separated and therefore the determined difference spectrum is appropriate.

It should be noted that the above-described embodiments are mere examples of the present invention, and it is obvious that even if appropriate modifications, additions and modifications are added within the scope of the spirit of the present invention, it is encompassed within the claims of the present invention.

For example, although the above-described embodiment is applied to the data obtained by an LC-MS according to the present invention, in a GC-MS, an LC using a PDA detector or a UV-visible spectrophotometer capable of wavelength scanning, a GC using an infrared spectrophotometer as a detector, it is obvious that it can be applied to data constituting the spectrum which is sequentially obtained with the lapse of time. Further, in the imaging mass spectrometer, the present invention can also be used in processing data obtained from a large number of measurement points having different spatial positions.

DESCRIPTION OF REFERENCE SYMBOLS

1: LC unit
2: MS unit
3: data processing unit
31: data collection processing unit
32: data storage unit
33: principle component analysis processing unit
34: characteristic spectrum acquisition unit
35: spectrum similarity calculation unit
36: difference spectrum determination unit
37: component identification unit
38: spectrum library
4: input unit
5: display unit

The invention claimed is:

1. A three-dimensional spectral data processing device configured to process three-dimensional spectral data constituted with a plurality of spectrums each indicating a relationship between a first parameter and a signal intensity and obtained in accordance with a change in a second parameter, the three-dimensional spectral data processing device being configured to analyze similarity or difference between respective three-dimensional spectral data obtained from a plurality of samples, the plurality of samples comprising a plurality of specific samples and a plurality of nonspecific samples, the three-dimensional spectral data processing device comprising:
  a) a characteristic spectrum acquisition unit configured to perform multivariate analysis in which a plurality of spectrums constituting three-dimensional spectral data obtained from one of the plurality of specific samples are considered as a collection of spectrums independent of a value of the second parameter, and to obtain, based on a result of the multivariate analysis, one or a plurality of characteristic spectrums that characterize the one of the plurality of specific samples;
  b) a spectrum similarity calculation unit configured, for each of the plurality of samples, to calculate a similarity value between each spectrum corresponding to each of a plurality of values of the second parameter extracted from the three-dimensional spectral data of the corresponding sample and the one or the plurality of characteristic spectrums obtained by the characteristic spectrum acquisition unit and, for each of the one or the plurality of characteristic spectrums of the corresponding sample, to calculate a representative similarity value corresponding to the sample from the plurality of similarity values; and
  c) a difference spectrum determination unit configured to check whether or not there is a significant difference capable of distinguishing the plurality of specific samples from the plurality of nonspecific samples based on the representative similarity value and to determine the characteristic spectrum responsible in obtaining the significant difference as a difference spectrum.

2. The three-dimensional spectral data processing device as recited in claim 1, further comprising:
a database that stores information on compounds; and
a component identification unit configured to perform component identification by collating information obtained from the difference spectrum determined by the difference spectrum determination unit with information in the database.

3. The three-dimensional spectral data processing device as recited in claim 1, further comprising:
a display configured to display the difference spectrum determined by the difference spectrum determination unit and a distribution status of the representative similarity value in all samples for the difference spectrum.

4. A three-dimensional spectral data processing method configured to process three-dimensional spectral data constituted with a plurality of spectrums each indicating a relationship between a first parameter and a signal intensity and obtained in accordance with a change in a second parameter, the three-dimensional spectral data processing method being configured to analyze similarity or difference between respective three-dimensional spectral data obtained from a plurality of samples, the plurality of samples comprising a plurality of specific samples and a plurality of nonspecific samples, the three-dimensional spectral data processing method comprising:
a) a characteristic spectrum acquisition step of performing multivariate analysis in which a plurality of spectrums constituting three-dimensional spectral data obtained from one of the plurality of specific samples are considered as a collection of spectrums independent of a value of the second parameter, and based on a result of the multivariate analysis, obtaining one or a plurality of characteristic spectrums that characterize the one of the plurality of specific samples;
b) a spectrum similarity calculation step of calculating, for each of the plurality of samples, a similarity value between each spectrum corresponding to each of a plurality of values of the second parameter extracted from the three-dimensional spectral data of the corresponding sample and the one or the plurality of characteristic spectrums obtained in the characteristic spectrum acquisition step and, calculating, for each of the one or the plurality of characteristic spectrums of the corresponding sample, a representative similarity value corresponding to the sample from the plurality of similarity values; and
c) a difference spectrum determination step of checking whether or not there is a significant difference capable of distinguishing the plurality of specific samples from the plurality of nonspecific samples based on the representative similarity value and determining the characteristic spectrum responsible in obtaining the significant difference as a difference spectrum.

5. The three-dimensional spectral data processing method as recited in claim 4, further comprising:
a component identifying step of performing component identification by collating information obtained from the difference spectrum determined in the difference spectrum determining step with information in database containing information on compounds.

6. The three-dimensional spectral data processing method as recited in claim 4, further comprising:
a display processing step of displaying the difference spectrum determined in the difference spectrum determining step and a distribution status of the representative similarity value in all samples for the difference spectrum by a display unit.

* * * * *